(12) United States Patent
Dasgupta et al.

(10) Patent No.: US 8,501,808 B2
(45) Date of Patent: Aug. 6, 2013

(54) FOAM ENHANCEMENT OF FATTY ACYL GLYCINATE SURFACTANTS

(75) Inventors: Bivash Ranjan Dasgupta, Hamden, CT (US); Prabhjyot Singh, Stratford, CT (US); Kavssery Parameswaran Ananthapadmanabhan, Woodbury, CT (US); Prem Chandar, Closter, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 342 days.

(21) Appl. No.: 12/834,061

(22) Filed: Jul. 12, 2010

(65) Prior Publication Data

US 2012/0009127 A1 Jan. 12, 2012

(51) Int. Cl.
*A01N 37/12* (2006.01)
*A01N 37/44* (2006.01)
*A61K 31/195* (2006.01)

(52) U.S. Cl.
USPC ........................................ 514/561

(58) Field of Classification Search
None
See application file for complete search history.

(56) References Cited

U.S. PATENT DOCUMENTS

| | | | |
|---|---|---|---|
| 7,282,471 B2 | 10/2007 | Harichian et al. | |
| 7,659,233 B2 | 2/2010 | Hurley et al. | |
| 2006/0019844 A1 * | 1/2006 | Aubrun-Sonneville et al. | 510/127 |
| 2006/0088495 A1 * | 4/2006 | Harichian et al. | 424/70.28 |
| 2006/0089277 A1 | 4/2006 | Harding et al. | |
| 2007/0053853 A1 | 3/2007 | Hurley | |
| 2007/0232508 A1 * | 10/2007 | Oshimura | 510/130 |
| 2007/0280976 A1 | 12/2007 | Taylor et al. | |
| 2008/0008668 A1 | 1/2008 | Harichian et al. | |
| 2008/0299053 A1 * | 12/2008 | Yang et al. | 424/54 |

FOREIGN PATENT DOCUMENTS

| | | |
|---|---|---|
| EP | 0648833 A1 | 4/1995 |
| EP | 1000606 A2 | 5/2000 |
| EP | 2184051 A1 | 5/2010 |
| FR | 2939658 | 6/2010 |
| JP | 1233264 | 9/1989 |
| JP | 07109498 A * | 4/1995 |
| JP | 2006273816 | 10/2006 |
| WO | 96/35410 | 2/2006 |
| WO | WO2006026875 A1 | 3/2006 |
| WO | WO2009071776 A2 | 6/2009 |
| WO | WO2011020679 A1 | 2/2011 |
| ZA | 7103553 | 2/1972 |

OTHER PUBLICATIONS

Mamada et al., 1989, Antimicrobial Characteristics and Adsorption to Halogenated Glycerine, Bokin Bobai Abstract, vol. 17, No. 9, 413-418.
International Search Report PCT/EP2011/061185 dated Mar. 21, 2012.

* cited by examiner

Primary Examiner — James H Alstrum Acevedo
Assistant Examiner — Thor Nielsen
(74) Attorney, Agent, or Firm — Karen E. Klumas

(57) ABSTRACT

A personal care cleansing composition is provided which includes a $C_{10}$-$C_{24}$ acyl glycinate salt and a dihydroxypropyl quaternary ammonium salt. Most preferred is sodium cocoyl glycinate in combination with dihydroxypropyl trimethyl ammonium chloride. The quaternary ammonium salt enhances foaming properties of the glycinate salt.

4 Claims, No Drawings

FOAM ENHANCEMENT OF FATTY ACYL GLYCINATE SURFACTANTS

BACKGROUND OF THE INVENTION

1. Field of the Invention

The invention relates to personal care cleansing compositions containing $C_{10}$-$C_{24}$ acyl glycinates with enhanced foaming properties.

2. The Related Art

Personal care cleansing compositions are products such as shampoos, bodywash, liquid and bar type hand cleansers, and even toothpastes. Common to these products are surfactant systems. Consumers perceive efficacy of these products in terms of the volume and richness of foaming during use. Limp foam is consumer unacceptable.

Mildness is another attribute that consumers expect of their cleansing products. Chemists are challenged to deliver on both attributes. Among effective and inexpensive foaming surfactants are the sulfates and sulfonates. Alkyl sulfates and sulfonates, as well as their ethoxylated derivatives are the surfactant work horses of personal care cleansing. They are inexpensive but definitely not mild.

A stable of more skin friendly surfactants is available to the chemist. Among these are the $C_{10}$-$C_{24}$ acyl glycinates. These materials have a desirable skinfeel and are mild, not causing any perceptible irritation. Besides a cost factor, acyl glycinates have only modest foamability.

WO 96/35410 (Henkel) reports use of dihydroxypropyl trimethylammonium chloride salts formulated into shampoos. These compositions further contain zwitterionic surfactants such as cocoalkyl dimethylammonium glycinate. These zwitterionic glycinates are different from the anionic glycinates of the present invention.

There is evident need for mild non-irritating surfactant systems that nevertheless have enhanced foaming properties.

SUMMARY OF THE INVENTION

A personal care cleansing composition is provided which includes:
(i) from about 1 to about 20% of a $C_{10}$-$C_{24}$ acyl glycinate salt of the formula (I)

(I)

wherein R is a $C_9$-$C_{23}$ alkyl group, and X is a cation selected from the group consisting of sodium, potassium, ammonium and triethanolammonium ions; and
(ii) from about 0.05% to about 10% by weight of a dihydroxypropyl quaternary ammonium salt of structure AB, wherein
A is a cationic charged component of the salt AB,
B is an anionic charged component of the salt AB, and
A has a single quaternized nitrogen atom, at least two hydroxyl groups and a molecular weight no higher than about 250.

DETAILED DESCRIPTION OF THE INVENTION

Now it has been found that dihydroxypropyl quaternary ammonium salts have ability to enhance foaming of $C_{10}$-$C_{24}$ acyl glycinate surfactants.

Accordingly, a first element of the present invention is that of a $C_{10}$-$C_{24}$ acyl glycinate salt. These salts are represented by the formula (I)

(I)

wherein R is a $C_9$-$C_{23}$ alkyl group, and X is a cation selected from the group consisting of sodium, potassium, ammonium and triethanolammonium ions.

Amounts of the glycinate salt may range from about 1 to about 20%, preferably from about 3 to about 15%, and optimally from about 5 to about 10% by weight of the composition. Most preferred among the glycinate salts is cocoyl glycinate salt, more particularly sodium cocoyl glycinate.

Enhancement of foaming is achieved through use of a dihydroxypropyl quaternary ammonium salt in combination with the glycinate salt. The dihydroxypropyl quaternary ammonium salt has structure AB, wherein A is a cationic charged component of the salt AB, B is a an anionic charged component of the salt AB, and A has a single quaternized nitrogen atom, at least two hydroxyl groups and a molecular weight no higher than about 250 but preferably no higher than about 200, and optimally no higher than 170.

Anionic charged component B may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate. The number and charge of negatively charged component B will be sufficient to neutralize the positive charge of component A.

A preferred embodiment of the quaternary ammonium salts is the dihydroxypropyl tri($C_1$-$C_3$ alkyl or hydroxyalkyl) ammonium salts.

These salts may be obtained in a variety of synthetic procedures, most particularly by hydrolysis of chlorohydroxypropyltri($C_1$-$C_3$ alkyl or hydroxyalkyl) ammonium salts. Ordinarily the $C_1$-$C_3$ alkyl or hydroxyalkyl constituent on the quaternized ammonium group will be methyl, ethyl, n-propyl, isopropyl, hydroxyethyl, hydroxymethyl and mixtures thereof. Particularly preferred is a trimethyl ammonium group known through INCI nomenclature as a "trimonium" group. Especially useful for the present invention is dihydroxypropyltri($C_1$-$C_3$ alkyl) ammonium salts. Most effective is 2,3-dihydroxypropyltrimethylammonium chloride.

Amounts of the dihydroxypropyl quaternary ammonium salts may range from about 0.05 to about 10%, preferably from about 0.1 to about 10%, more preferably from about 0.5 to about 10%, optimally from about 1 to about 10% by weight of the composition.

Advantageously the pH of compositions of this invention may range from about pH 5.5 to 8, preferably from 6 to 7.5, and optimally from 6.8 to 7.5.

Compositions of the present invention ordinarily will contain water. These compositions may also include a hydrophobic phase thereby being an emulsion. Water-in-oil and oil-in-water as well as triplex emulsions may be useful as carriers according to the present invention. Amounts of water may range from about 10% to about 95%, preferably from about 30 to about 85%, and optimally from about 50 to about 70% water by weight of the composition.

Co-surfactants may also be included in the compositions. These may be in amounts ranging from about 0.1 to about 30%, preferably from about 1 to about 20%, and optimally from about 1 to about 10% by weight of the composition, and being highly dependent upon the type of personal care cleansing product.

The co-surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include salts of the following: fatty acids (i.e. soap), alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Humectants may be present in the compositions. These are generally polyhydric alcohol-type materials. Typical polyhydric alcohols include glycerin, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from about 0.2 to about 40%, preferably between 1 and 25%, most preferably between 2 and 15% by weight of the composition. Most preferred is glycerin as an humectant or moisturizer.

Emollient materials may be formulated into the compositions. These may be natural or synthetic esters and hydrocarbons. Amounts of the emollients may range anywhere from about 0.1 to about 20%, preferably between about 1 and about 10% by weight of the composition.

Among the ester emollients are:
(a) Alkyl esters of saturated fatty acids having 10 to 24 carbon atoms. Examples thereof include behenyl neopentanoate, isononyl isonanonoate, isopropyl myristate and octyl stearate.
(b) Ether-esters such as fatty acid esters of ethoxylated saturated fatty alcohols.
(c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
(d) Wax esters such as beeswax, spermaceti wax and tribehenin wax.
(e) Sugar ester of fatty acids such as sucrose polybehenate and sucrose polycottonseedate.

Natural ester emollients principally are based upon mono-, di- and tri-glycerides. Representative glycerides include cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons suitable for the compositions include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as components. Illustrative of this category are pelargonic, lauric, myristic, palmitic, stearic, isostearic, oleic, linoleic, linolenic and behenic acids.

Sunscreen agents may also be included in compositions of the present invention. Particularly preferred are such materials as ethylhexyl p-methoxycinnamate, available as Parsol MCX®, Avobenzene available as Parsol 1789®, and benzophenone-3 also known as Oxybenzone. Inorganic sunscreen actives may be employed such as microfine (1 to 100 nm) titanium dioxide and zinc oxide. Amounts of the sunscreen agents when present may generally range from 0.1 to 30%, preferably from 2 to 20%, optimally from 4 to 10% by weight of the composition.

Structurants for aqueous compositions may be selected from inorganic water structurants, charged polymeric water structurants, water soluble polymeric structurants, associative water structurants, and mixtures thereof. Non-limiting examples of inorganic water structurants include silicas, polymeric gellants such as polyacrylates, polyacrylamides, starches, modified starches, crosslinked polymeric gellants, copolymers, and mixtures thereof. Non-limiting examples of charged polymeric water structurants include Acrylates/Vinyl Isodecanoate Crosspolymer, Acrylates/C10-30 Alkyl Acrylate Crosspolymer, Carbomers, Ammonium Acryloyldimethyltaurate/VP Copolymer, Ammonium Acryloyidimethyltaurate/Beheneth-25 Methacrylate Crosspolymer, Acrylates/Ceteth-20 Itaconate Copolymer, Polyacrylamide, and mixtures thereof. Non-limiting examples of water soluble polymeric structurants include cellulose gums and starches. Non-limiting examples of associative water structurants include xanthum gum, gellum gum, pectins, alginates such as propylene glycol alginate, and mixtures thereof.

Cationic deposition polymers may also be utilized. Non-limiting examples include polysaccharide polymers, such as cationic cellulose derivatives. Preferred are the salts of hydroxyethyl cellulose reacted with trimethyl ammonium substituted epoxide, referred to the industry as polyquaternium T10 which are available from Amerchol Corp. in their Polymer KG, JR and LR series of polymers.

Toothpastes formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 1800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Colorants, opacifiers and abrasives may also be included in compositions of the present invention. Each of these substances may range from about 0.05 to about 5%, preferably between 0.1 and 3% by weight of the composition.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Example 1

Experiments were conducted to evaluate foamability of aqueous formulas containing either sodium cocoyl glycinate or 2,3-dihydroxypropyl trimethylammonium chloride, or combinations of these two materials. The Rotating Cylinder Test was employed for the evaluation. The test involved pouring a 5 ml sample at 1/10 dilution into a 25 ml cylinder. The aqueous systems were adjusted to a pH of approximately 7. The stoppered cylinder was placed into a mechanical rotator and rotated at 50 rpm for 1 minute. Rotation was stopped and, 30 seconds thereafter, lather volume in the cylinder was recorded. Results are reported in Table I below.

TABLE I

| Sample No. | Sodium Cocoyl Glycinate (wt %) | Dihydroxypropyl Trimethylammonium Chloride (wt %) | Foam Height (ml) | % Change in Foam Height |
|---|---|---|---|---|
| A | 5 | — | 10.63 | 0.0 |
| B | 5 | 1 | 12.19 | 14.7 |
| C | 5 | 5 | 12.69 | 19.4 |
| D | 5 | 10 | 11.81 | 11.2 |
| E | — | 5 | 0.00 | 0.0 |

Samples B, C and D demonstrate that dihydroxypropyltrimethylammonium salts enhance the foaming properties of sodium cocoyl glycinate.

Examples 2-4

A series of shower gel formulas suitable for the present invention are recorded in Table II below.

TABLE II

| | Example (wt %) | | |
|---|---|---|---|
| Ingredients | 2 | 3 | 4 |
| Ammonium Laureth-3 Sulfate | 3.0 | 3.0 | 3.0 |
| Sodium Lauroamphoacetate | 16.7 | 16.7 | 16.7 |
| Sodium Cocoyl Glycinate | 10.0 | 8.0 | 6.5 |
| Lauric Acid | 0.9 | 0.9 | 0.9 |
| Trihydroxystearin | 2.0 | 2.0 | 2.0 |
| Guar Hydroxypropyltrimonium Chloride | 0.17 | 0.75 | 0.75 |
| Polyquaterium 10 | 0.45 | — | — |
| Polymethacrylamidopropyltrimonium Chloride | — | 0.24 | — |
| Polyquaternium-39 | — | 0.81 | — |
| PEG 90M | 0.25 | — | — |
| PEG-14M | 0.45 | 2.45 | 2.45 |
| Linoleamidopropyl PG-Dimonium Chloride | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| 2,3-Dihydroxypropyl Trimethylammonium Chloride | 1.0 | 2.0 | 0.3 |
| Glydant ® DMDM Hydantoin | 0.37 | 0.37 | 0.37 |
| Citric Acid | 1.6 | 0.95 | 0.95 |
| Water | Balance | Balance | Balance |

Example 5

A shampoo composition useful in the context of the present invention is described in Table III below.

TABLE III

| Ingredient | Weight % |
|---|---|
| Ammonium Laureth Sulfate | 12.00 |
| Ammonium Lauryl Sulfate | 2.00 |
| Cocoamidopropyl Betaine | 2.00 |
| Sodium Cocoyl Glycinate | 5.00 |
| 2,3-Dihydroxypropyl Trimethylammonium Chloride | 0.50 |
| Glycerin | 5.00 |
| Dihydroxypropyltrimonium Chloride | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® Preservative | 0.0008 |
| Benzyl Alcohol | 0.0225 |
| Water | Balance |

Example 6

An aerosol packaged foaming cleanser useful in the context of the present invention is described in Table IV.

TABLE IV

| Ingredient | Weight % |
|---|---|
| Sodium Cocoyl Glycinate | 10.00 |
| Glycerin | 10.00 |
| Maleated Soybean Oil | 5.00 |
| Silicone Urethane | 1.00 |

TABLE IV-continued

| Ingredient | Weight % |
| --- | --- |
| Polyglycero-4 Oleate | 1.00 |
| Sodium C14-16 Olefin Sulfonate | 15.00 |
| Sodium Lauryl Ether Sulphate (25% Active) | 15.00 |
| Cocoamidopropylbetaine | 15.00 |
| DC 1784 ® (Silicone Emulsion 50%) | 5.00 |
| Polyquaternium-11 | 1.00 |
| Dihydroxypropyltrimonium Chloride | 1.00 |
| Water | Balance |

Example 7

A toilet bar illustrative of the present invention is outlined under Table V.

TABLE V

| Ingredient | Weight % |
| --- | --- |
| Sodium Soap (85/15 Tallow/Coconut) | 67.77 |
| Sodium Cocoyl Glycinate | 10.00 |
| Dihydroxypropyltrimonium Chloride | 3.50 |
| Dimethicone | 2.00 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

Example 8

A foaming toothpaste according to the present invention can be formulated with the ingredients listed under Table VI.

TABLE VI

| Ingredient | Weight % |
| --- | --- |
| Zeodent 115 ® | 20.00 |
| Glycerin | 18.00 |
| Xanthan Gum | 7.00 |
| Sodium Carboxymethyl Cellulose | 0.50 |
| Sodium Bicarbonate | 2.50 |
| Dihydroxypropyltrimonium Chloride | 2.00 |
| Sodium Cocoyl Glycinate | 1.50 |

TABLE VI-continued

| Ingredient | Weight % |
| --- | --- |
| Sodium Fluoride | 1.10 |
| Sodium Saccharin | 0.40 |
| Titanium Dioxide | 1.00 |
| Pluronic F-127 ® | 2.00 |
| FD&C Blue No. 1 | 3.30 |
| Menthol | 0.80 |
| PEG-10 Dimethicone | 0.50 |
| Water | Balance |

The foregoing description illustrates selected embodiments of the present invention. In light thereof, variations and modifications will be suggested to one skilled in the art, all of which are within the spirit and purview of this invention.

What is claimed is:

1. A personal care cleansing composition comprising:
   (i) from about 3 to about 15% of a cocoyl glycinate salt of the formula (I)

wherein R is a $C_9$-$C_{23}$ alkyl group, and X is a cation selected from the group consisting of sodium, potassium, ammonium and triethanolammonium ions; and
   (ii) from about 1% to about 10% by weight of a dihydroxypropyl quaternary ammonium salt of structure AB, wherein
   A is a cationic charged component of the salt AB,
   B is an anionic charged component of the salt AB, and
   A has a single quaternized nitrogen atom and a molecular weight no higher than 250, and
   wherein the dihydroxypropyl quaternary ammonium salt is 2,3-dihydroxypropyl trimethylammonium chloride.

2. The composition according to claim 1 wherein the glycinate salt is sodium cocoyl glycinate.

3. The composition according to claim 1 which has a pH ranging from about 5.5 to 8.

4. The composition according to claim 1 wherein the glycinate salt is present in an amount from about 5 to about 10% by weight of the composition.

* * * * *